United States Patent [19]

Thierry

[11] Patent Number: 6,096,335
[45] Date of Patent: Aug. 1, 2000

[54] STABLE PARTICULATE COMPLEXES HAVING A LAMELLAR, ROLLED, AND CONDENSED STRUCTURE

[75] Inventor: Alain R. Thierry, L'Union, France

[73] Assignee: Biovector Therapeutics, S.A., Labege Cedex, France

[21] Appl. No.: 09/126,402

[22] Filed: Jul. 30, 1998

[30] Foreign Application Priority Data

Jul. 30, 1997 [FR] France ................................ 97 09698
Aug. 29, 1997 [FR] France ................................ 97 10812

[51] Int. Cl.[7] ............................. A61K 9/127; B32B 9/02; C12N 15/88
[52] U.S. Cl. ................. 424/450; 428/402.2; 428/402.24; 435/458
[58] Field of Search ........................... 435/458; 424/450; 428/402.2, 402.24

[56] References Cited

U.S. PATENT DOCUMENTS 5,622,712  4/1997  Eppstein et al. .
5,676,954  10/1997  Brigham .
5,908,777  6/1999  Lee et al. ............................. 435/320.1

FOREIGN PATENT DOCUMENTS

WO 91/17424  11/1991  WIPO .
WO 97/04748  2/1997  WIPO .
WO 97/30170  8/1997  WIPO .
WO 98/02144  1/1998  WIPO .
WO 96/03977  2/1998  WIPO .

OTHER PUBLICATIONS

Behr, "Gene Transfer with Synthetic Cationic Amhiphiles: Prospects for Gene Therapy" Bioconjugate Chem. 5, 382–389 (1994).
Felgner et al., "Nomenclature for Synthetic Gene Delivery Systems" Human Gene Therapy 8, 511–512 (Mar. 20, 1997).
Felgner et al., Lipofection: A Highly Efficient, Lipid-Mediated DNA-Transfection Procedure: Proc. Natl. Acad. Sci. USA 84, 7413–7417 (Nov. 1987).
Gao et al., "A Novel Cationic Liposome Reagent for Efficient Transfection of Mammalian Cells" Biochemical and Biophysical Research Communications 179, 280–285 (Aug, 30, 1991).
Hofland et al., "Formation of Stable Cationic Lipid/DNA Complexes for Gene Transfer" Proc. Natl. Acad. Sci. USA 93, 7305–7309 (Jul. 1996).
Lee, et al., "Folate-targeted, Anionic Liposome-entrapped Polylysine-condensed DNA for Tumor Cell-specific Gene Transfer" Journal of Biological Chemistry 271, 8481–8487 (1996).
Nicolau, et al., "Liposomes as Carriers for in Vivo Transfer and Expression" Method in Enzymology 149, 157–176 (1987).
Thierry, et al., "Systemic Gene Therapy: Biodistribution and Long-Term Expression of a Transgene in Mice" Proc. Natl. Acad. Sci. USA 92.
Xu et al., "Mechanism of DNA Release from Cationic Liposome/DNA Complexes Used in Cell Transfection" Biochemistry 35, 5616–5623 (1996).
Zhu et al., Systemic Gene Expression After Intravenous DNA Delivery into Adult Mice: Science *261*, 209–211 (Jul. 9, 1993).

*Primary Examiner*—Terry McKelvey
*Attorney, Agent, or Firm*—Hoffmann & Baron, LLP; Irving N. Feit

[57] ABSTRACT

This invention concerns stable particulate complexes with a neutral or negative global charge of lamellar structure made consisting of at least one globally anionic biologically active substance and mixture of a cationic constituent and an anionic constituent. The invention also concerns unilamellar vesicles for preparation of these complexes as well as their preparation and utilisation.

35 Claims, 6 Drawing Sheets

STABLE PARTICULATE COMPLEXES HAVING A LAMELLAR, ROLLED, AND CONDENSED STRUCTURE

This invention concerns particulate complexes resulting from the association of biologically active substances with vesicles useful as vectors of active substances. It also concerns the utilisation of vesicles appropriate for the formation of these complexes as well as compositions including these complexes. Finally, the invention concerns the preparation of these vesicles and complexes and compositions containing them.

Many systems for the vectorisation of active substances are already known, such as liposomes, nanoparticles, polymer particles, immuno- and ligand-complexes and cyclodextrins (Drug Transport in antimicorbial and anticancer chemotherapy. G.Papadakou Ed. CRC Press, 1995).

However, none of these systems has proved to be truly satisfactory for the in vivo transport of nucleic acids such as, for example, deoxyribonucleic acid (DNA). This shortcoming is one of the problems addressed by the technique known as gene therapy (R. G. Crystal, Science, 270, 404–410, 1995). Gene therapy is the transfection of a nucleic acid-based product, such as a gene, into the cells of an organism. The gene is expressed in the cells after it has been introduced into the organism.

Several methods of cell transfection exist at present. These methods can be grouped as follows:
use of calcium phosphate or polycations, microinjection, protoplasmic fusion;
electroporation and injection of free DNA.
viral infection;
synthetic vectors.

Methods in the first group are not applicable to in vivo transfection. As a result, most initial clinical trials of gene therapy taking place today are based upon the utilisation of retroviral and adenoviral vectors. These vectors are effective in stably transfecting heterologous genes into cells for expression. However, clinical utilisation of vectors of viral origin appears problematic because of their potential toxicity.

DNA viruses such as adenoviruses or herpes virus are potential transporters of DNA, but cause problems related to immunogenicity, toxicity and production costs.

Electroporation and injection of free DNA, offer a useful alternative, but are relatively ineffective, and limited to local administration only.

There is increasing interest in the use of synthetic vectors such as lipid or polypeptide vectors, since this strategy appears to be less toxic than the viral vectors. The genetic material to be delivered is usually a plasmid (pDNA), the production of which is easy and inexpensive. The plasmid, which is usually produced in bacteria, contains not only the gene, but also sequences ensuring cis control of regulation of the expression of the gene. The common control sequences include promoters, enhancer sequences, operative sequences, ribosomal attachment sites, initiation codons, end of transcription signals, and polyadenylation signals. Other DNA sequences can also be inserted, such as buffer sequences, replication origin sites, homologous recombination sites or introns.

In general, the transport of nucleic acids (NA) is limited by their major biodegradability. pDNA in particular must be delivered totally intact to the nucleus of the target cell to enable expression of the transgene. The pDNA pathway after systemic administration involves many stages, each of which is a potential barrier to transgene expression:

transport in circulating blood from the injection site to target tissues/cells;

diffusion from the intravascular compartment to the extravascular compartment, also referred to as extravasation in tissues, and entry into cells;

release of synthetic vector particles/pDNA or of free pDNA in the cytoplasmic compartment;

separation of pDNA from synthetic vectors;

transfer from cytoplasm to nucleus;

nuclear penetration;

transgene expression.

The following are the characteristics of an optimal transport system for gene transfer:

Acquisition of synthetic vector particles/homogeneous DNA of small size enabling condensation (i.e. rendering more compact)of DNA.

Protection of DNA against nucleases.

Acquisition of particles with an improved plasma half-life, via decreasing interactions with blood cells or plasma proteins.

Transport of DNA in the target cell.

Release of DNA in cytoplasm and nucleoplasm.

Cell targetting ability.

Among synthetic vectors, lipid vectors and liposomes appear to have the advantage over polypeptide vectors of being potentially less immunogenic and, for the time being, of being more efficient. However, the use of conventional liposomes for DNA delivery is very limited because of the low encapsulation rate and their inability to compact large molecules, such as nucleic acids.

The formation of DNA complexes with cationic lipids has been studied recently by many laboratories (Felgner et al., PNAS 84, 7413–7417 (1987); Gao et al., Biochem. Biophys. Res. Commun. 179, 280–285, (1991); Behr, Bioconj. Chem. 5, 382–389 (1994)). These DNA-cationic lipid complexes have also been designated in the past using the term lipoplexes (P. Felgner et al., Hum. Genet. Ther., 8, 511–512, 1997). Cationic lipids enable the formation of electrostatic complexes with DNA, which is a poylanionic substance.

The use of cationic lipids has been shown to be effective in the transport of pDNA in cell culture. However, the in vivo application of these complexes, particularly after systemic administration, for gene transfer, is poorly documented (Zhu et al., Science 261, 209–211 (1993); Thierry et al., PNAS 92, 9742–9746 (1995); Hofland et al., PNAS 93, 7305–7309 (1996)).

Nevertheless, this type of administration is of essential interest in certain medical applications. The explanation lies in the difficulty of obtaining complexes that are of homogeneous size and structure, and that are relatively stable to biodegradation. Patent application WO 96/03977 of the National Institutes of Health, for example, refers to liposomes usable for DNA delivery in vitro, made up of cationic lipids and neutral lipids. However, the overall cationic nature of these liposomes combined with pDNA is a notable limitation of this type of system for some applications.

Up to now, it was impossible to obtain stable and homogeneous lipoplexes that have a neutral or negative global charge, and that would be effective for cell transfection. The reactions used in the formation of lipoplexes involve the formation of electrostatic bonds between polyanionic constituents. The formation of such bonds are difficult to control.

It is recognised that positive particles bind effectively and non-specifically to serum proteins, most of which have a negative global charge. Such binding leads to the inactivation and rapid plasma elimination of the proteins, leading to increased toxicity and, potentially, an inflammatory reaction. Furthermore, positively charged particles interact positively with extracellular matrixes and, as a result, show limited extravasation from the vascular space to the interstitial space.

The cationic nature of lipoplexes developed in the past is a severe limitation to their utilisation by systemic administration. This partially explains the wide divergence between efficacy in vitro and that in vivo.

It is of interest, in this respect, to note that lipoplexes already developed are not effective for muscle cell transfection after intramuscular injection, but that HVJ liposomes are (Yanagihara et al., Gene Ther. 3, 549–557 (1996)). HVJ (Hemagglutinin Virus of Japan) liposomes are neutral liposome preparations, the membranes of which contain inert particles of HVJ virus and which encapsulate pDNA previously encapsulated with HMG1 histones. This system has proved to be effective for various applications in vilvo. Its clinical application, however, appears seriously limited, because of immunogenicity and toxicity problems related to the presence of viral particles. The reasons for the superior efficacy in muscle cells of HVJ liposomes in comparison with that of cationic lipid vectors could be explained by better endosomal release and the neutral charge.

It has also been shown (H. Komatsu et al., BBA 1235, 270–280) (1995) that certain non-aqueous hydrophilic solvents, e.g. ethanol, modify the ultrastructure of lipid membranes that form liposome membranes. In an aqueous solvent, the fatty acid chains of the lipids form bilayers, wherein the hydrophobic tails of the fatty acids in one of the layers juxtapose the hydrophobic tails of the other layer, leaving a space between the two layers. By solubilizing the lipids with an appropriate dilution of a non-aqueous, hydrophilic solvent in an aqueous solution, the fatty acids in one layer interact and intermingle with the hydrophobic tails of the other layer, thereby increasing membrane fluidity. Vesicles that contain such modified bilayers can be described as being "interdigitated." These membranes are also less thick than the lipid bilayers that form in aqueous solvents(<60 Angstroms) and have a unilamellar appearance like that of SUVs (Small Unilamellar Vesicles).

In the past, active substances have been encapsulated in vesicles, without structural rearrangement. Applicants' research has enabled him to prepare vesicles particularly suitable for the formulation of anionic biological substances such as DNA, and hence to obtain stable complexes, enabling transportation of these biological substances as part of vectors for medical purposes. In this specification, biological substances that are part of vectors will be said to be vectorised.

The invention concerned here is designed to provide a transport system for active agents, and nucleic acids in particular, free of the disadvantages of earlier systems. The formulation of the invention notably enables optimal gene transfer, since it offers the advantages listed below which form the basis of effective transfection:

Condensation of DNA.
Protection of DNA against nucleases.
Improved plasma half-life, via decreased interaction with blood cells or plasma proteins.
Transport in DNA target.
Release of DNA in cytoplasm and nucleoplasm.
Cell targeting ability.

SUMMARY

This goal is achieved by providing a stable, particulate complex having a spherical shape and a lamellar, rolled and condensed particulate structure, the complex comprising a globally anionic biologically active substance and a mixture of a cationic constituent and an anionic constituent, wherein at least one of the cationic constituent and the anionic constituent is a lipid. In a preferred embodiment, the complex has a global negative or neutral charge. In another embodiment, the complexes further comprise a neutral constituent.

Figure 1A:
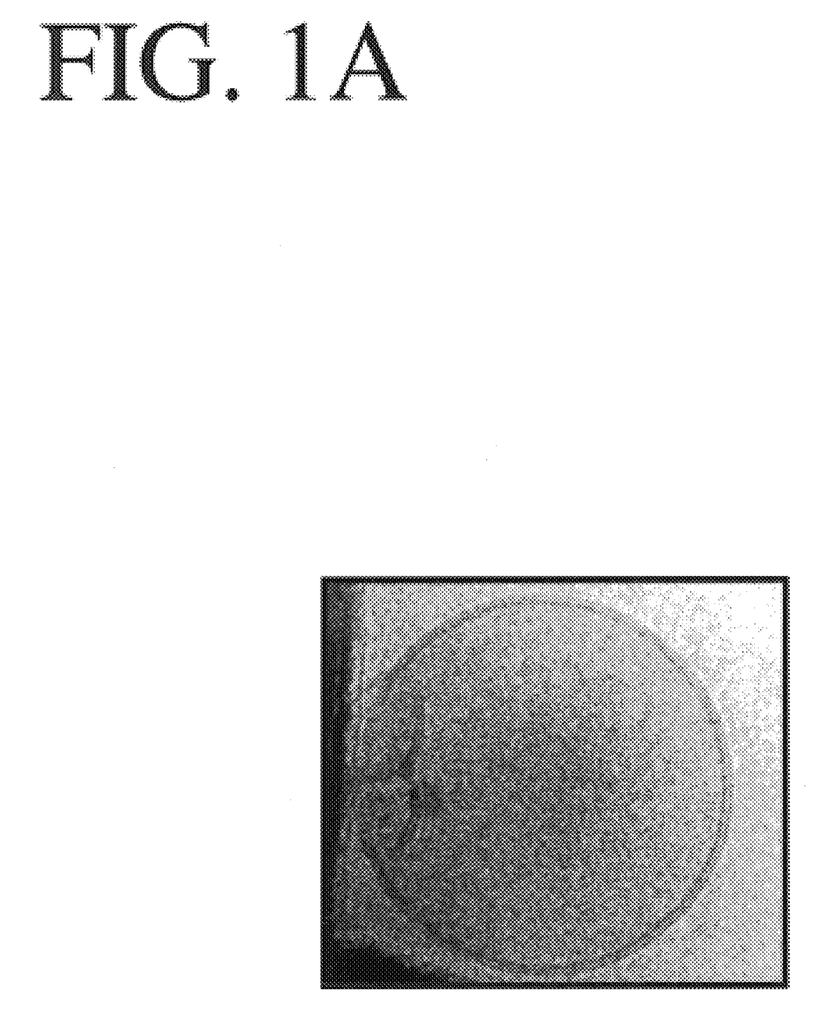
FIGS. 1A and 1B are microphotographs of the ultrastructure of Nx2D vesicles and Nx2D/pDNA complexes, respectively, by cryoelectron microscopy. The scale bar is 50 nm.
Figure 1B:
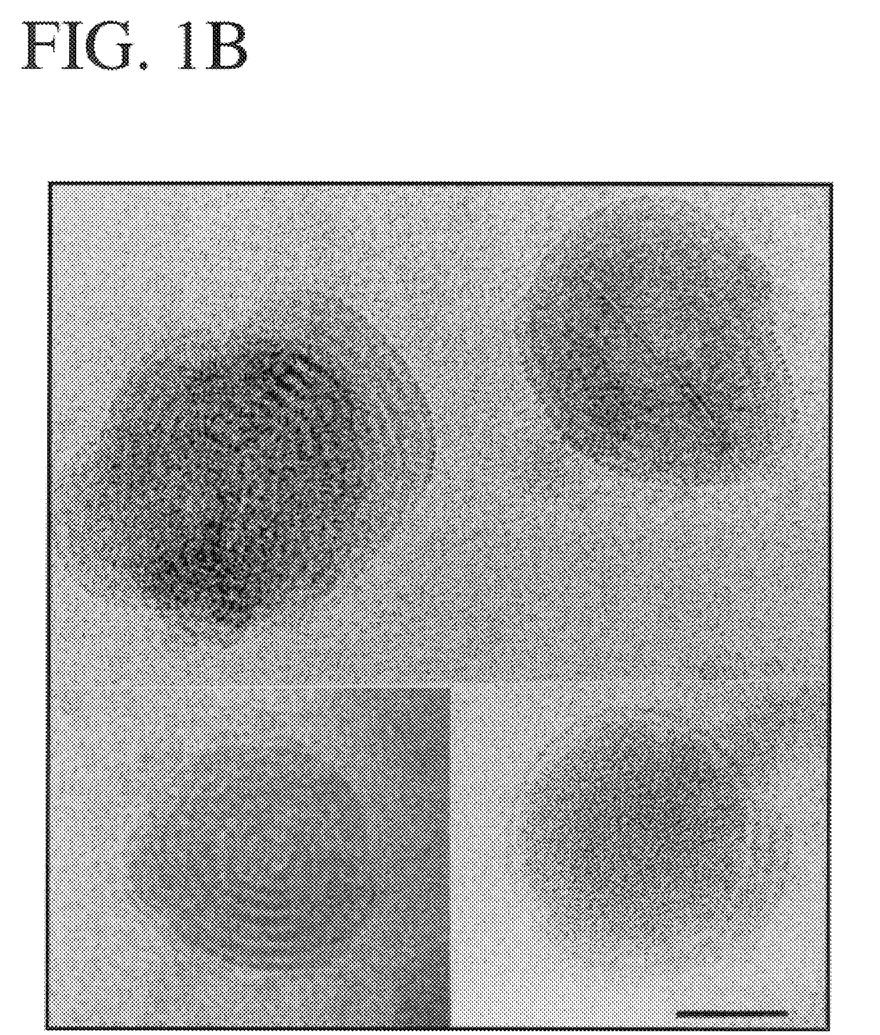
Figure 1C:
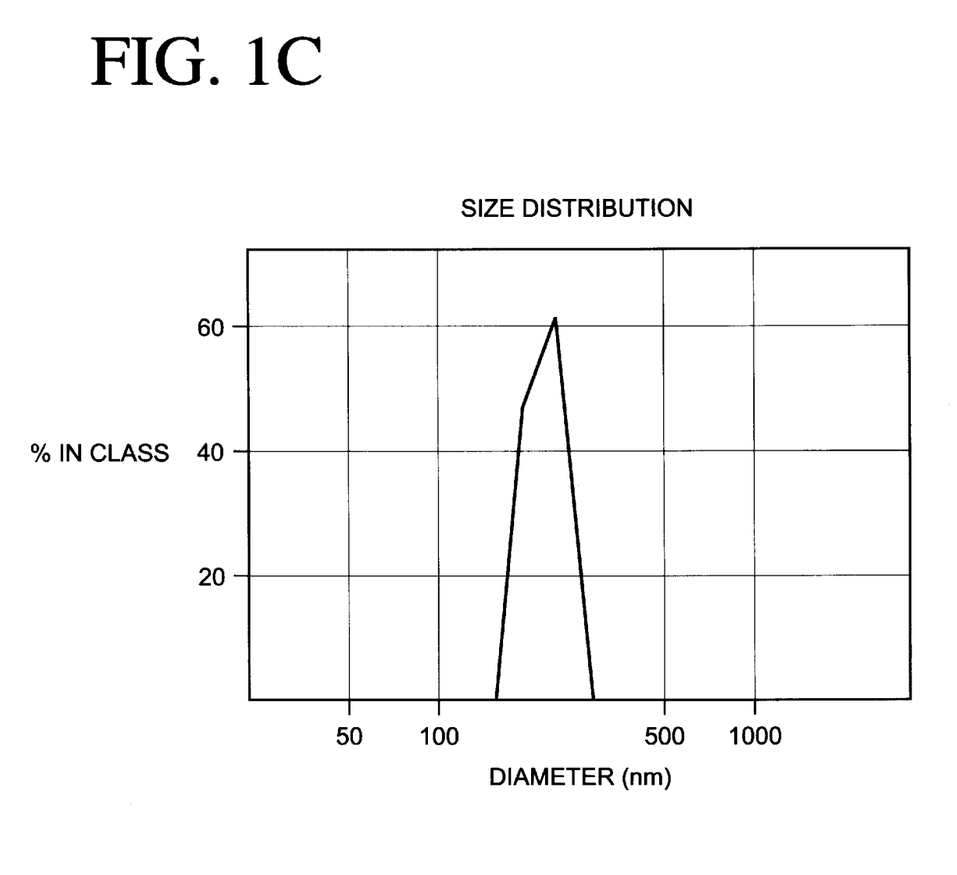
FIG. 1C shows the size distribution of Nx2D/pDNA complexes as determined by dynamic light scattering.
Figure 2A:
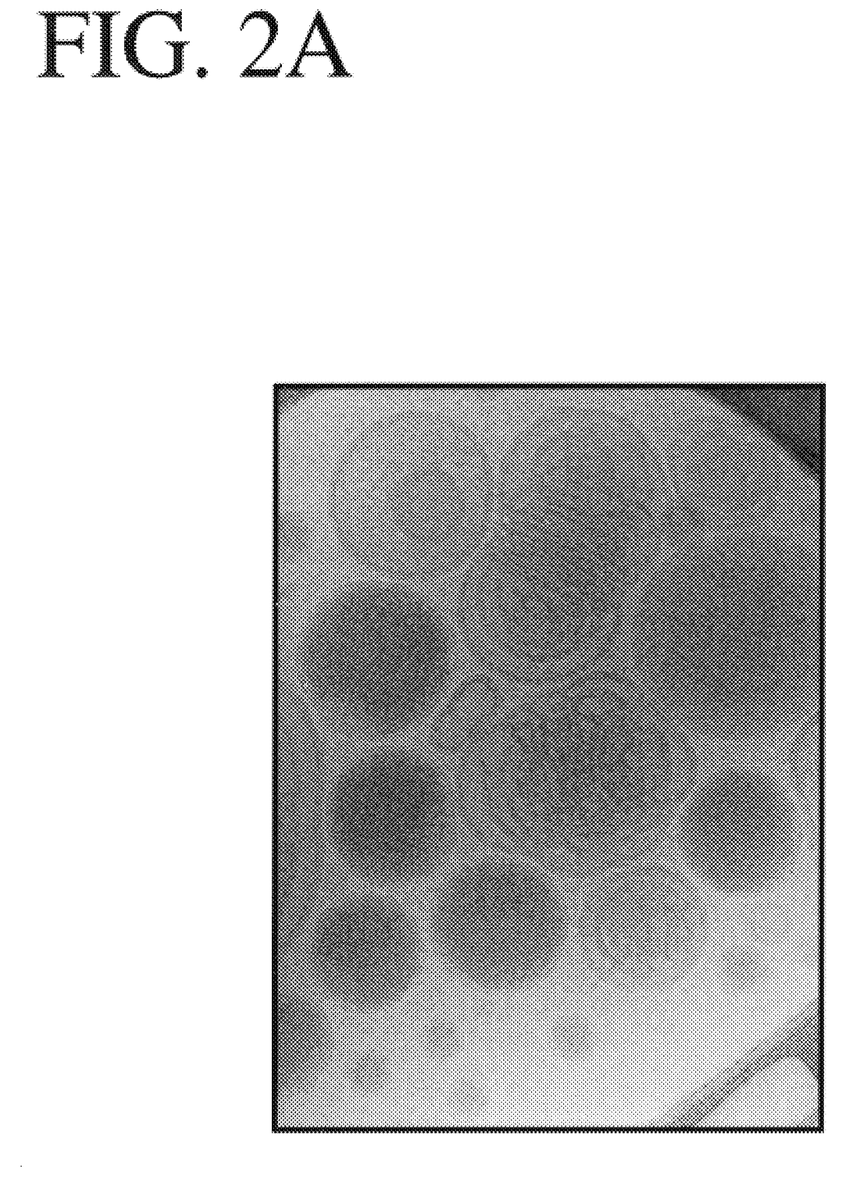
FIG. 2A shows a cryoelectron microscopy image of a Neutraplex™ formed with the long double stranded DNA of the T4 phage virus.
Figure 2B:
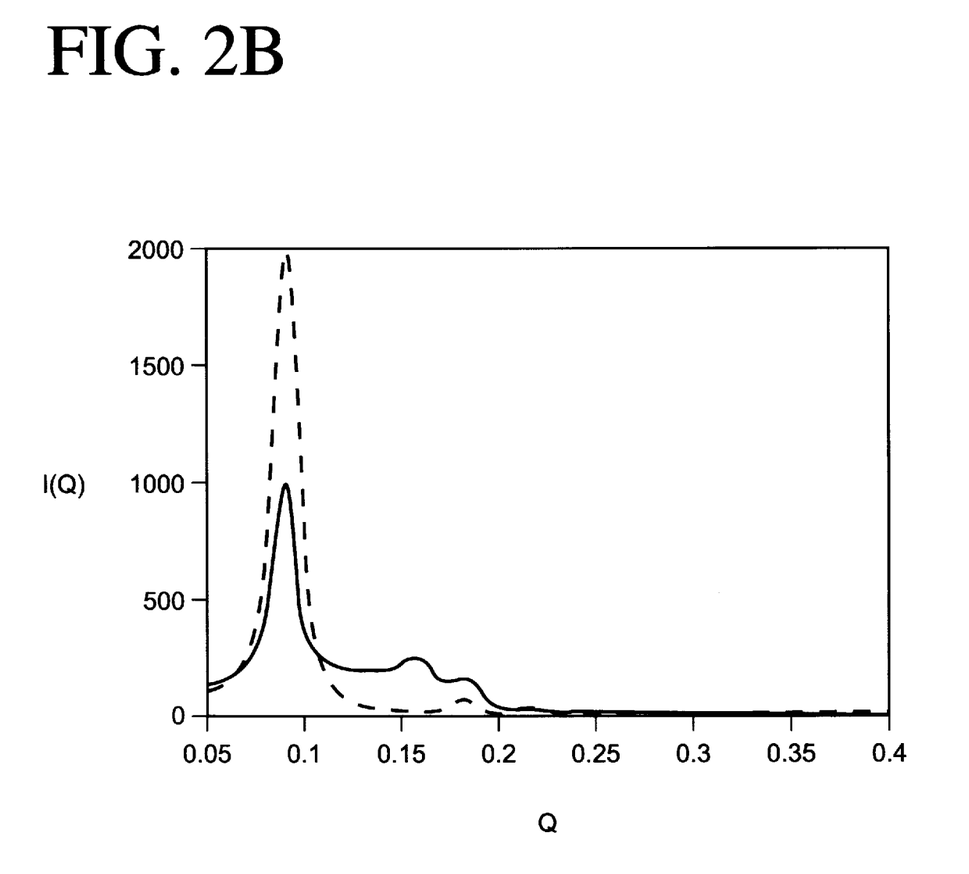
FIG. 2B shows a small angle X-ray analysis (SAXS) of Nx2D/pDNA (dotted line) and Nx/T4 DNA (full line).
Figure 3:
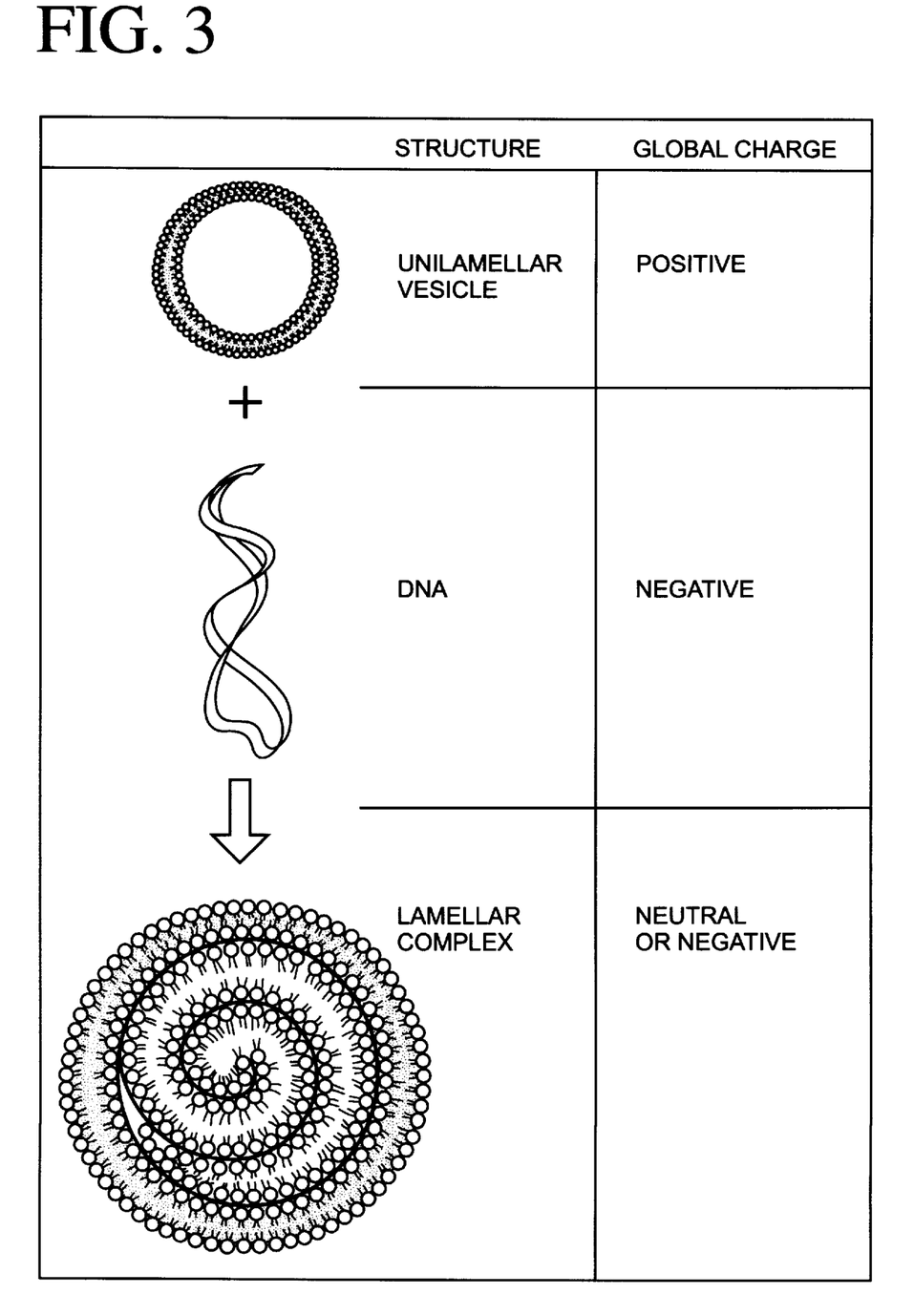
FIG. 3 is a diagram showing the structure and preparation of Neutraplex™ complexes.

The complexes of the invention provide a system for the vectorisation of active substances in particulate form. The complexes will be referred to below as Neutraplex™ (Nx) complexes. In comparison with previously available complexes, Neutraplex™ complexes are lipoplexes that are stable, and have a condensed particulate structure that is spherical in shape, as shown in FIGS. 1 and 2. The Neutraplex™ complexes have an orderly liquid crystalline structure that exhibits a lamellar, rolled arrangement.

The complexes may have a positive, neutral or negative global charge. The complexes preferably have a neutral or negative global charge.

The system of the invention is remarkable in that it enables disposition of the particulate complex of neutral or negative global charge, offering the advantage of being able significantly to condense DNA, such as pDNA; and being fusogenic (e.g. able to disrupt intracellular membranes, such as, for example, endosomal membranes). Generally speaking, it is preferable to use a delivery system that is substantially neutral or weakly negative, since for systemic administration the delivery yield of the active substance at its site of action is greatly improved in comparison with a positively charged system, which is limited regarding its biodistribution and toxicity. The negative global charge or substantial neutrality of the complex lowers pharmacological and physiological barriers and, in particular, improves transport in tissue cell matrix, or, under some circumstances, enhances extravasation. Alternatively, complexes with positive global charge are, under some circumstances, advantageous, for example for parenteral/local administration.

DESCRIPTION OF THE FIGURES

FIGS. 1A–1C.

FIGS. 2A–2B.

DETAILED DESCRIPTION

In this specification, all numbers are approximate, unless otherwise stated or required by the context in which the number is used. The words "comprising," "comprise," "comprises," and the like mean "including, but not limited to." The words "consisting of," "consist of," "consists of," and the like mean "including and limited to."

One of the advantages of the complexes of the invention is condensation, i.e. making more compact, of the vectorised biologically active substance. This goal is preferably achieved in particular with a cationic constituent that has anionic substance condensation properties.

The biologically active substance involved in the composition of the particulate complexes of the invention is preferably a nucleic acid, and the invention also envisages more paticularly that the cationic constituent should be a substance with DNA condensation properties, but any cationic compound is acceptable in the context of the invention, e.g. histones, spermines or spermidines. Preference is nevertheless shown for a cationic constituent of lipid nature. Any lipid with a positive overall charge is suitable. Some preferred positively charged lipids include lipomonoamines such as DOTAP and DOTMA, lipopolyamines such as DOGS and DOSPA, and phosphonolipids such as dioleoyl-trimethylammonium phosphonolipid and mirystoyltrimethylammonium phosphonolipid. DOTAP: 1-2-dioleoyloxy-3(trimethylamino)propane, DOTMA: N[1-(2,3-dioleoyloxy)propyl]-N,N,N-trimethylammonium chloride, DOGS: dioctadecylamidoglycilspermine, DOSPA: 2,3-dioleoyloxy-N(2-sperminecarboxamido)ethyl-N,N-dimethyl-1-propanaminium trifluoroacetate.

As a result of the special method of production of the complexes of the invention, the cationic constituent can be non-lipid if the anionic constituent is a lipid. Constituents of a non-lipid nature include polymers, such as polypeptides, lipopeptides, polysaccharides, chitosan, polylysine, polyethyleneimine, and cationic detergents, such as, for example, CTAB, which are also known for their ability to compact DNA.

The anionic constituent involved in the composition of the particulate complexes of the invention should preferably also be a lipid, more preferably a phospholipid. Any lipid with a negative overall charge, such as phosphatidylserine or phosphatidylinositol and their derivatives, is acceptable in the context of the invention.

Particular preference is shown for Cardiolipin or its natural or synthetic derivatives as anionic constituent. Cardiolipin is a natural diphosphatidylglycerol that can be extracted from mammalian heart, and that contains approximately 90% C18:2 and 9% C18:1. It is available from Avanti Polar Lipids Incorporated of Alabaster, Ala., U.S.A. and from Sigma-Aldrich Fine Chemicals. See, for example, Lipids 6, 260–265 (1965).

However the anionic constituent of the complexes of the invention can also be non-lipid if the cationic constituent is a lipid. Some examples of suitable non-lipid anionic constituents include polymeric compounds, such as, for example, polyglutamic acid, or anionic detergents, such as, for example, lysophosphatidylglycerol.

When the active substance is a nucleic acid, it is particularly preferable that the anionic constituent should be a lipid comprising mainly a diphosphatidylglycerol, e.g. Cardiolipin or one of its synthetic analogues or derivatives. Although Cardiolipin is fusogenic, the complex of the invention preferably includes a neutral lipid, e.g. another fusogenic lipid, such as phosphatidyl ethanolamine or its derivatives, e.g. dioleylphosphatidyl ethanolamine (DOPE). The complexes of the invention then have the fusogenic property essential for the release of DNA from endosomes to cytoplasm.

Furthermore, a neutral constituent, such as a neutral lipid, e.g. cholesterol or DOPE, can participate in stabilisation of the structure of the complexes of the invention. This neutral constituent can also be a zwitterionic lipid compound such as sphingomyelin, which may have a fusogenic potential in the complexes of the invention.

Hence the DNA transport system involved in this invention is preferably a unique combination of one or more, or all, of the following properties essential for obtaining an optimal DNA vector:
preferably of exclusively lipid nature, hence minimally immunogenic;
good DNA condensation, ensuring cellular penetration of DNA;
fusogenicity;
highly structured membrane nature.

In a preferred complex of the invention, applicants propose for the first time association of an anionic constituent with a cationic constituent so as to obtain a vesicle that condenses nucleic acids while ensuring the preparation of stable complexes with a negative or neutral global charge possessing the properties mentioned above.

The global charge of the complexes of the present invention is the result of the relative number of positive to negative charges, and can be measured in terms of their charge ratios. In this specification, charge ratios are defined in accordance with Feigner et al., Human Gene Therapy 8, 511–512 (1997) as:

$$\text{Charge ratio} = \frac{\text{Positive charge equivalents of total cationic components}}{\text{Negative charge equivalents of total anionic components}}$$

The total cationic components comprise cationic constituents, such as cationic lipids. The total anionic components comprise anionic constituents, such as anionic lipids, and the globally anionic biologically active substance.

The complexes of the present invention may be positive, but are preferably negative. Preferably, the complexes have charge ratios of approximately 0.01–10, more preferably of approximately 0.01–1.0, and most preferably of approximately 0.01–0.9. For example, a Neutraplex™ formulation containing 1 mg DOGS (3 positive charges/molecule, 1263 MW), 1 mg DOPE (0 electric global charge), 0.5 mg Cardiolipin (2 negative charges/molecule, 1573 MW) have a theoretical charge ratio of 2.14 and 0.68 when adding 10 and 60 ug of pDNA (1 negative charge/340 g), respectively. Experimentally, the zeta potential, expressed as mV is indicative of the particle charge ratio. The zeta potential can be determined by a zeta potential analyzer.

It is preferable for the membranes of the complexes of the invention to have no components that cause undesirable side effects, other than particles of the active substance. Undesirable side effects include, for example, unwanted immunogenicity or toxicity. It is particularly preferable for the membranes of the complexes of the invention to have no viral particles, such as, for example, HVJ particles.

Active substances combined with vesicles in the complexes of the invention are preferably biological or chemical substances with a biological effect and preferably with therapeutic, prophylactic (i.e. vaccinal) or diagnostic properties.

The invention is aimed in particular at active substances that are globally negative compounds or polyanions. Some preferred examples include double or single stranded nucleic acid molecules, viral genomes, parts of viral genomes procaryote genomes, parts of procaryote genomes, chromosomes, or parts of chromosomes. Some examples of nucleic acid molecules include DNA or RNA sequences, oligonucleotides, and ribozymes. Other compounds may also enter into the complexes of the invention, e.g. other polyanions such as heparin and gangliosides, or globally negative compounds chosen from among proteins, peptides, lipoproteins, glycolipids, hormones, nucleosides and vitamins as well as their conjugates. The system of the invention enables vectorisation of at least one biologically active substances. It is also possible to prepare complexes associating several biologically active substances, chosen in particular from among those mentioned above, in one lamellar particle.

The system of the invention is particularly suitable for the transport of nucleic acids. The active substance may, for example, be a DNA coding for a protein, such as those chosen in the following group: cell mediators (e.g. cytokines, growth factors, chemokines and interleukines, etc.), transcription factors, membrane proteins, viral proteins and epitopes, blood clotting factors, hormones etc.

The complexes of the invention are preferably of the size that can flow easily in small blood vessels of mammals, such as humans. Accordingly, the complexes of the invention are preferably less than 400 nm in size.

The invention also covers compositions made up of identical or different complexes, as described above, in a medium compatible with the active substance, i.e. a pharmaceutically acceptable medium, and which ensures retention of the neutral or negative overall charge of the complexes of the invention.

In a preferred embodiment, cationic or neutral unilamellar vesicles with an interdigitated membrane are used in the preparation of the neutral or globally anionic complexes of the invention. For the purposes of this specification, an interdigitated membrane is a lipid membrane in which the hydrophobic tails of the lipid molecules are not head-to-head, but are interconnected. In other words, the hydrophobic tails in the membrane bilayer no longer face each other. The space between the adjacent tails has been significantly eliminated, and the tails mingle with each other, thereby increasing membrane fluidity. The membranes are made up of a cationic constituent, an anionic constituent, and, optionally, a neutral constituent. At least one of the cationic and anionic constituents is preferably a lipid.

The vesicles of the invention are advantageously small in size and made up of interdigitated and/or SUV (Small Unilamellar Vesicles) membranes, with a positive or neutral global charge.

The vesicles of the invention are particularly intended to be used in the composition of the complexes defined above, and as a result have the characteristics stated when describing the complexes. As a result, the cationic constituent is a substance that condenses anionic substances.

Preferably, the cationic constituent is a lipid. When the active agent to be complexed with the vesicles of the invention is a nucleic acid molecule, such as DNA or RNA, it is particularly preferable that the cationic constituent should be a substance that condenses nucleic acid molecules. Suitable cationic constituents include, for example, lipomonoamines and lipopolyamines, as mentioned above.

However, the cationic constituent can also be non-lipid if the anionic constituent is a lipid. Non-lipid cationic constituents, as mentioned above, include, in particular, cationic polypeptides or polysaccharides.

Similarly, it is preferable that the anionic constituent should also be a lipid, preferably a phospholipid, and in this situation the invention specifically envisages Cardiolipin and its natural or synthetic derivatives. But the anionic constituent can also be non-lipid if the cationic constituent is a lipid. When present, the neutral constituent is preferably a neutral lipid, such as DOPE.

The invention hence also concerns compositions including identical or different vesicles of the invention in a compatible medium.

The invention also covers the preparation of the above vesicles and complexes, as well as compositions containing them.

The neutral or negative complexes of the preferred embodiment of the invention are obtained by using a particular type of vesicle described above and a process for their formulation, together with use of a composition including the anionic substance This process and composition are aimed at solving, amongst others, the problem created by the addition of the anionic substance to a preparation of stable vesicles of homogeneous structure. It is known (Y. Xu, F. C. Szoka, Biochem. 35, 5616–5623, 1996) that the addition of an anionic substance such as an anionic phospholipid greatly disturbs the stability of the complex via competition regarding electrostatic interaction between the cationic lipid and a polyanion such as a nucleic acid.

Preparation of the complexes and vesicles of the invention is characterised by the fact that the cationic constituent and anionic constituent, at least one of which is a lipid, preferably a phospholipid, are dispersed in one or more non-aqueous, hydrophilic, polar solvents, before or during mixing for preparation of the vesicles of the invention.

The non-aqueous solvent can be protic or aprotic, and is preferably water soluble.

Some suitable examples of protic solvents include alcohols having 1–4, preferably 2–3, carbon atoms. The preferred alcohols are ethanol and isopropanol. Other examples of protic solvents include ethylene glycol, propylene glycol, and glycerol. Some examples of aprotic solvents include dimethyl sulfoxide, acetonitrile and acetone.

The non-aqueous, hydrophilic, polar solvents may contain up to approximately 50%, preferably up to approximately 40%, and more preferably up to approximately 30% water. In general, solvents for lipid constituents advantageously contain very little, if any, water, e.g. 0–5%, preferably 0–3%, more preferably 0–2%, and most preferably 0–1%. Solvents for some hydrophobic polymeric constituents advantageously contain approximately 10–20% water.

More particularly, the process for preparation of complexes according to the invention involves the following steps:

a) A cationic constituent and an anionic constituent, at least one of which is preferably a lipid, and more preferably a phospholipid, are mixed together. The cationic and anionic constituents may be either dispersed separately in identical or different solvents and then mixed, or added and dispersed together in a solvent. The solvent is a non-aqueous, hydrophilic, polar solvent.

b) An excess of an aqueous solution, such as an aqueous salt or buffer solution is added.

c) At least one globally anionic biologically active substance in solution, preferably an aqueous solution, is added to the above mixture.

In a preferred version of the above process, step (a) comprises mixing in a solvent a cationic constituent with an anionic constituent, at least one of these constituents being a lipid, preferably a phospholipid.

More preferably, both the cationic and anionic constituents are lipids. In this situation, the vesicles of the invention are preferably prepared with approximately 0.1 to 5% (w/w) of lipids in relation to solvent, which favours the formation of supramolecular complexes with anionic compounds, such as DNA.

Special preference is shown for use of a non-aqueous, hydrophilic, polar solvent for mixing the cationic and anionic constituents at step (a) of the process, and preferably a alcoholic solvent, such as ethanol.

Conveniently, these cationic and anionic constituent are mixed in a molar ratio of between 0.1:2 and 10:1.

The aqueous solution added at step (b) preferably consists of water, and is added to the mixture of the cationic and anionic constituents in a proportion of about 100 to 2000 μl per mg.

In a preferred application of the process of the invention, the mixture of step (a) is prepared and kept until step (b) at a temperature of about 30 to 50° C.

The process of the invention may also include the addition of a neutral constituent, preferably a lipid, at step (a).

In a process in accordance with the invention where the globally anionic biologically active substance in solution is chosen from among double or single strand nucleic acids, chromosomes or parts of chromosomes, DNA or RNA sequences, oligonucleotides or antisense oligonucleotides and ribozymes, it is added at step (c) in a proportion of between about 10 and 500 μg per mg of the cationic and anionic constituents.

A preferred method of application of the process of the invention consists at step (a) of taking up a film of a cationic or anionic lipid with minimal volume of alcoholic solution of lipid with a charge opposite to that of the film and at its limit of solvatation.

When the film consists of a cationic lipid, step (a) of the process of the invention involves it being taken up with an alcoholic solution of an anionic lipid. On the contrary, when the film consists of an anionic lipid, step (a) of the process of the invention involves it being taken up with an alcoholic solution of an cationic lipid.

The solvent of the lipid with a charge opposite to that of the film of step (a) is chosen from among non-aqueous, hydrophilic, polar solvents such as alcohols having one to four carbon atoms, preferably ethanol and isopropanol, ethylene glycol, propylene glycol, glycerol, DMSO, acetone and acetonitrile.

The cationic, anionic, and neutral constituents used in the process of the invention are similar to those defined above for the complexes and vesicles of the invention.

The vesicles of the invention are prepared according to steps (a) and (b) of the process described above. In order to keep the lowest possible ethanol/lipoplex ratio for pharmacological toxicity reasons, while retaining the properties of the solvent for membrane fluidity, e.g. mobility, this invention proposes an optimal process for the preparation of the vesicles of the invention, including the following steps film dry DOGS in a vacuum;

dissolve this film with an alcoholic solution of Cardiolipin: step (a) above;

heat to a tepid temperature to perfect and ensure complete dissolution;

add an excess of water: step (b) above.

More precisely, 1 mg of DOGS, optionally dried, is dissolved in 50 μl of a 10 mg/ml ethanolic solution of Cardiolipin. The preferable cationic constituent (DOGS)/anionic constituent (Cardiolipin) ratio is of the order of 0.05 to 10 (W/W).

Neutraplex™ complexes can be prepared extemporaneously from vesicle preparations stored at 4° C. after step (b). Ideally, the biologically active substances, more particularly a nucleic acid, is added to vesicles at concentrations of the order of 10 to 500 μg per mg of vesicles and 10 to 2000 μg/ml of final preparation.

Preparations derived from this invention can be obtained by addition during at least one of steps (a) to (c) or after step (c) of compounds with properties known to improve the transport potential of lipoplexes in general:

Stabilisation of membrane structure, e.g. with cholesterol.

Increasing plasma circulation, e.g. with PEG-based derivatives (polyethyleneglycol).

Cell targetting by addition of ligands or antibodies.

Protection of DNA structure, e.g. with histones or nucleoproteins.

Unrolling of DNA for transcription, e.g. with topoisomerase or other transcription factors.

Adding polyanions such as oligodeoxynucleotides or polycations such as polylysine.

A remarkable aspect of the process of the invention involves the use of a non-aqueous, hydrophilic, polar solvent during formulation. The preferred solvent is ethanol. Apart from its solvent properties, the non-aqueous, hydrophilic, polar solvent is also useful as a detergent playing a surfactant role. The non-aqueous, hydrophilic, polar solvent facilitates mobility in the hydrophobic interior of lipid membranes and is held in the lipid bilayer made up of a cationic compound and an anionic compound. When the active substance is a nucleic acid, the non-aqueous, hydrophilic, polar solvent also appears to facilitate the sliding and enveloping of the highly anionic nucleic acid on the cationically charged outer and inner surfaces of the bilayer of vesicles in a thermodynamic equilibrium.

The globally anionic biologically active substance, most commonly a nucleic acid, then condenses the lipid bilayer and associates itself with the two polar surfaces, reorienting the polar parts of the membrane towards the polyanionic chain. This leads to a spontaneous self-assembly reaction resulting in a new stable structure, called a Neutraplex™ The globally anionic biologically active substance forms an integral part of the particulate structure of the Neutraplex™.

In the prior art, neutral and negatively charged lipoplexes and polyplexes have been described in the prior art. In contrast to the Neutraplex™, however, the prior art lipoplexes and polyplexes were formed with mere aggregation. On the other hand, the Neutraplex™ is formed from a sudden and spontaneous change in the initially liposomal (unilamellar) particulate structure, which enters a liquid crystalline phase, and becomes a lamellar, rolled and condensed particulate structure, spherical in shape, and stable, as shown in FIGS. 1 and 2.

In other words, the complexes of the invention have a spherical shape. The spherical shape has a helical microstructure comprising coiled layers of the polyanion associated with the polar surfaces of the mixture of the cationic and anionic constituents.

The liquid crystalline phase of the complexes according to the invention, may sometimes exhibit as well a hexagonal structure. Furthermore, both lamellar and hexagonal phases may coexist in the same particle (FIG. 1B). The length and type of the anionic drug may influence the transition between the two phases. The structure of the complex according to the invention might corresponds to the 3-D hexagonal crystaline phase of DNA, such as found in virus phages (M. E. Cerritelli et al., Cell 91, 271–280(1997); (J. Lepault, J. Dubochet, W. Baschong, E. Kellenberger, the EMBO J. 6, 1507–1512(1987). The hexagonal phase is prone to fuse with the membranes of the target cell and to deliver intracellularly the biological compounds, while the lamellar phase is prone to condense and efficaciously protect the biological compounds.

Thus, by increasing membrane fluidity, the non-aqueous, hydrophilic, polar solvent facilitates the thermodynamic equilibrium leading to the creation of this particulate structure despite the opposing ionic forces of the various constituents, and provides neutral or negative lipoplexes (Neutraplex™ complexes). Some suitable non-aqueous, hydrophilic, polar solvents are mentioned above. The preferred solvent is ethanol. In addition to Cardiolipin, which is prone to form a hexagonal phase, the solvent helps in obtaining the hexagonal liquid crystalline phase in Neutraplex™ complexes.

As an example of the stability achieved by the process described in this specification, the Neutraplex™ particles as prepared in example 2 are stable even following concentration of the materials. After dialysis in dextran, a stable Neutraplex™ preparation containing 1 mg/ml pDNA and 7.8 mg/ml lipids was obtained. In addition, equivalent or higher transfection efficiency can be achieved in cell culture in the presence of serum than can be achieved in the absence of serum.

It is also possible to make particles according to the invention by using a cationic constituent or a mixture of a cationic constituent and a neutral constituent, i.e. in the absence of an anionic constituent.

Other advantages and characteristics of the invention emerge from the examples given below concerning the preparation and utilisation of the complexes and vesicles of the invention:

EXAMPLES

Example 1

Preparation of Nx1D Vesicles with the Composition DOGS/Cardiolipin 1 mg of DOGS cationic lipopolyamine solubilised in ethanol is evaporated to dryness in a rotating round-bottomed borosilicated glass tube. The dry lipid film obtained is resuspended in 50 µl of a solution of Cardiolipin in ethanol (10 mg/ml). The DOGS/Cardiolipin ratio is 1/0.5. Resuspension is favoured by gentle shaking and heating the tube in a bath at 30–35° C. for 15 min. 350 µl of deionised sterile water are then quickly added to the lipid solution and the mixture gently stirred by whirlimixer. The preparation can be stored at 4° C.

Example 2

Prepation of Nx1D/pDNA Neutraplex™ with the Composition DOGS/Cardiolipin/pDNA

A preparation of DOGS/Cardiolipin prepared as described in Example 1 is diluted in a 150 nM NaCl solution (25 µl of preparation in 50 µl of 150 mM NaCl solution) and left at room temperature for 15 min. Thirty µg of pDNA diluted in a buffer (60 µl) are quickly added to the preparation and the mixture gently shaken then homogenized. The lipoplex preparation thus obtained is incubated for one hour at room temperature and stored at 4° C. The complexes obtained have a neutral charge: these are Neutraplex™ complexes.

Example 3

Preparation of Nx2D Vesicles with the Composition DOGS/DOPE/Cardiolipin 1 mg of DOGS cationic lipopolyamine and 1 mg of DOPE solubilised in ethanol are evaporated to dryness in a rotating round-bottomed borosilicated glass tube. The dry lipid film obtained is resuspended in 50 µl of a solution of Cardiolipin in ethanol (10 mg/ml), the DOGS/DOPE/cardiolipin weight ratio being 1/1/0.5. Resuspension is favoured by gentle shaking and heating the tube in a bath at 30–35° C. for 15 min. 350 µl of deionised sterile water are then quickly added to the lipid solution and the mixture gently stirred by whirlimixer. The preparation can be stored at 4° C.

Example 4

Preparation of Nx2D/pDNA Neutraplex™ with the Composition DOGS/DOPE/Cardiolipin

A preparation of DOGS/DOPE/Cardiolipin prepared as described in Example 3 is diluted in a 150 nM NaCl solution (25 µl of preparation in 50 µl of 150 mM NaCl solution) and left at room temperature for 15 min. 30 µg of pDNA diluted in a buffer (70 µl) are quickly added to the preparation and the mixture gently shaken then homogenized. The lipoplex preparation thus obtained is incubated for one hour at room temperature and stored at 4° C. The complexes obtained have a neutral charge. If more than 30 µg of pDNA are added, the complexes have a negative charge.

Example 5

Optimisation of the Formulation of Neutrapl™ Complexes

Several types of formulation have been tested to obtain a stable and homogeneous suspension of vesicles resulting from mixing together a cationic lipid (DOGS) and an anionic lipid (Cardiolipin=CL). The formulations compared are:

A=Lipid film suspension in water.
B=Lipid film suspension in ethanol.
C=Mixture of cationic and anionic lipids in an ethanolic solution.
D=Cationic lipid film suspension with an ethanolic solution of anionic lipid.

Table 5-1 below shows the results obtained with the above formulations using various lipids and a fixed DNA concentration of 30 µg of DNA/60 µg of DOGS.

TABLE 5-1

| Lipids | Lipids ratio | Vesicle formulation | Suspension of vesicles | Suspension of Neutraplex ™ Complexes |
|---|---|---|---|---|
| DOGS/CL | 1/1 | A | impossible | impossible |
| | | B | impossible | impossible |
| | 1/0.5 | A | impossible | impossible |
| | | B | aggregation | impossible |
| | | C | poor solubility | impossible |
| | | D | yes | yes |
| | 1/0.2 | A | impossible | impossible |
| | | D | yes | yes |
| | | C | yes | yes |
| DOGS/DOPB/CL | 1/1/1 | A | impossible | impossible |
| | | B | aggregation | impossible |
| | 1/1/0.5 | A | impossible | impossible |
| | | B | aggregation | impossible |
| | | D | yes | yes |
| | 1/1/0.2 | D | yes | yes |
| | 1/1/0.1 | D | yes | yes |

Table 5-1 shows that only formulation C and D, resulting from a mixture of cationic and anionic lipids in an ethanolic solution and the addition of Cardiolipin in an ethanolic solution (EtOH) to a dry film of cationic lipid, respectively, resulted in a suspension of vesicles and the formation of stable and homogeneous Neutraplex™ complexes.

Example 6

Particulate Analysis of the Complexes and Vesicles of the Invention

A laser-scattering analyser (dynamic light scattering) was used for particulate analysis.

Results obtained from compositions of vesicles prepared according to examples 1 (Nx1D) and 3 (Nx2D) and from Neutraplex™ complexes prepared according to the formulations described in example 2 (Nx1D/pDNA) and example 4 (Nx2D/pDNA) are shown in Table 6-1 below.

TABLE 6-1

| Formulation | Preparation | Mean z | Polydispersity |
|---|---|---|---|
| Nx1D | No 1 | 251 | 0.292 |
| | | 248 | 0.307 |
| | | 248 | 0.262 |
| | | Mean: 249 | Mean: 0.287 |
| Nx1D/pDNA | No 1 | 622 | 0.833 |
| | | 702 | 0.836 |
| | | 698 | 0.757 |
| | | Mean: 674 | Mean: 0.809 |
| Nx2D | No 1 | 197 | 0.351 |
| | | 195 | 0.378 |
| | | 197 | 0.367 |
| | | Mean: 197 | Mean: 0.365 |
| | No 2 | 152 | 0.3 |
| | | 151 | 0.318 |
| | | 153 | 0.316 |
| | | Mean: 152 | Mean: 0.311 |
| | No 2 1 month after preparation | 153 | 0.302 |
| | | 152 | 0.295 |
| | | 151 | 0.300 |
| | | Mean: 152 | Mean: 0.299 |
| NX2D/pDNA | No 1 | 353 | 0.386 |
| | | 397 | 0.513 |
| | | 349 | 0.413 |
| | | Mean: 366 | Mean: 0.417 |
| | No 2 | 262 | 0.260 |
| | | 257 | 0.276 |
| | | 261 | 0.258 |
| | | Mean: 260 | Mean: 0.265 |
| | No 2 1 month after preparation | 251 | 0.185 |
| | | 243 | 0.218 |
| | | 243 | 0.188 |
| | | Mean: 246 | Mean: 0.197 |

The mean z is the mean size in nanometers of the particle population.

The polydispersity coefficient provides an evaluation of the homogeneity of the particle population. In view of the nature of the vesicles of the invention, polydispersity less than 0.350 is considered to be acceptable.

Results show than Nx1D and Nx2D particulate preparations were of small mean size and formed a homogeneous population. Preparations of complexes comprising DNA were of larger mean size than preparations of vesicles, without DNA. Preparation Nx2D/pDNA and, to a lesser extent, preparation Nx1D/pDNA were of acceptable homogeneity. Preparations Nx2D and Nx2D/pDNA proved to be reproducible and very stable after 1 month's storage at 4° C.

Example 7

Ultrastructure of the Multilamellar Complexes

The use of cryo-Electron Microscopy (cryoEM) enables the visualization of DNA macromolecules in the Neutraplex™ structure in combination with other analytical methods, providing critical insight into the phenomena of DNA packaging in Neutraplex™ delivery particles.

A study of the Nx2D vesicle preparation according to example 3 showed the presence of liposomal type unilamellar spherical vesicles only (FIG. 1A). The thickness of the membrane of these vesicles (50 Angstroms) was less than that of classical liposomal particles (60 Angstroms) and suggested the existence of interdigitations due to rearrangement of lipids in the presence of alcohol.

Neutraplex™ complexes formed with the pBKd1 RSVluc pDNA (10.4 kbp) and vesicles prepared with DOGS, DOPE, and Cardiolipin were submitted to Cryo-EM. As shown in FIG. 1, cryoEM examination reveals spherical particles exhibiting two kind of structures: mostly (>80% of total particles) a multilamellar organization of sperulite-like pattern and in to a lesser extent (<20%) a punctate pattern. Distinguishing the former concentric ring motif and the number of concentric layers depends upon the spherical condensate observed. Typically 5 to 10 concentric shells are observed to surround a central area of a punctate pattern. No free SUV could be observed on the squares of the grids in FIG. 1B. All the complexes are highly sensitive towards the electron beams indicating high material density and also suggesting the presence of DNA. More precisely, cryoEM (FIG. 1B) revealed that the concentric ring pattern is made of alternative layers appearing transversely striated and of layers with low density. Based on the cryoEM images, the thickness of the striated layers has a mean value of 5.3 nm with a periodicity of 7.5 nm. The outer striated layer has a thickness of 4.1 nm. Perpendicular to these layers, faint striations can be seen mainly on the edge and also inside the particles. These striations are 2.0 nm thick with a periodicity of 3.4 nm (FIG. 1B).

Analysis by SAXS of an Nx2D/pDNA sample (FIG. 2B) revealed three diffraction peaks: one indicating a repetitive spacing of 2/0.094=6.9+/−1 nm and the second and fourth order indicating the multi-layer structure (2/0.18). The relative width of X-ray diffraction suggested highly ordered spherulite-like particles made of at least a dozen layers. Thus SAXS clearly confirmed the multilamellar structure of Nx2D/pDNA and the periodicity observed with cryoEM. Dynamic light scattering examination indicated a Neutraplex™ mean size of 254 nm (width: 108 nm) and exposed a monomodal population with a polydispersity of 0.193 (FIG. 2C). This spherulite structure with different packing regimes was also observed by cryoEM when using linear double strand DNA, single strand DNA and oligodeoxynucleotides (data not shown). It is noteworthy that the fraction of particles exhibiting a punctate array is greater (up to 50%) in Neutraplex™ formed with linear double strand DNA, single strand DNA. Such specific supramolecular organization is the result from thermodynamic forces, which cause compaction to occur through concentric winding of DNA in a liquid crystalline phase.

We have packaged T4 phage DNA (Sigma, St. Louis, USA) in Neutraplex™ by using the same formulation as before. CryoEM showed particles of spherical shape exhibiting a punctate array surrounded by a thin layer and lamellar particles (FIG. 2A). With fewer particles, we could observe the multilamellar structure as previously described in the case of Neutraplex™ composed of other DNA types tested here. As observed in cryoEM, the size distribution of these punctate T4 DNA filled particles have a mean diameter of 62 nm (n=38). At times, some elements of striation are barely detectable in Neutraplex™-T4 and T4 phage particles (FIG. 2A) SAXS patterns are completely different from those obtained for Neutraplex™-pDNA as shown in FIG. 2B. Three reflexions with spacing ratios of 1:3:4 in unit Q are observed. Two very weak reflexions with spacing radios of 1:7:9 are also sometimes detected (not visible on FIG. 2B). It indicates an hexagonal structure between parallel DNA chains surrounded by lipids. The parameters $a_H$ (spacing between two DNA molecules) of this hexagonal lattice seems to depend on specimens. Values ranging from 7 to 8 nm are found. Conversely, spherulite/concentric motif are the majority specie in Neutraplex™-pDNA cryoEM images corroborating with the lamellarity detected by SAXS. As punctate and multilamellar structure were associated in some lipoplex (Lx) particles both liquid crystalline and hexagonal phases may coexist in the same particle. As T4 DNA is more than 16 times longer than the pDNA used in this study, length and type of DNA might influence transition between both phases.

The cryoEM images of punctate Neutraplexrm particles formed with T4 DNA that we observe are strikingly similar to the images of phase lambda (Lepault et al.) complete tail-deletion mutant of T4 (Lepault et al.) and T7 phages (Cerittelli et al.) These T4-related phage particles showed a spherical shape and an average diameter of 80 nm[30]. Recent investigations (Lepault et al., Cerittelli et al.) performed by using tailless mutants, indicated DNA packing domains in viral particles. It is noteworthy that T7 tail-deletion mutants exhibit in cryoEM images a concentric ring motif as well as a punctate motif as observed for Neutraplex™ (Nx)-pDNA. Neutraplex™-T4 and -pDNA cryo-EM images and SAXS illustrate the structural transition of lamellar and hexagonal phases in Neutraplex™. This hexagonal liquid crystalline phase results from the use of a hydrophilic, non-aqueous solvent and compounds such as DOPE or Cardiolipin. Cerritelli et al. indicated that the state of DNA compaction in phage viral particles should correspond to the 3-D hexagonal crystalline phase of DNA. Nx1D-pDNA according to example 2 present as well the lamellar liquid crystalline phase. Cryo-EM observation of Neutraplex™es was made in salt containing media and reproducible up to at least three months.

This study provided evidence of the radical change in particle structure following the addition of DNA to the vesicles. The nucleo-lipid particulate complex obtained is not the result of simple aggregation but of supramolecular reassembly leading to stable particles with a defined and relatively homogenous structure.

Example 8

In vitro Transfection Using Neutraplex™ Complexes

Human embryonic kidney 293 cells, in half confluent culture, were exposed to a Nx2D/pGFP-DNA preparation (2µg). Plasmid pGFP-DNA codes for GFP (Green Fluorescent Protein) which is a fluorescent protein easily detectable in U.V. light 48 hours after 70 to 80% transfection of cells expressing GFP. The level of transfection was equivalent when the same Nx2D/pDNA preparation was used three weeks after storage at 4° C.

Example 9

Expression of Human Factor IX in Mouse Blood Following Intravenous Administration Using the Neutraplex™ System.

Human Factor IX gene (hFIX) inserted in an expression plasmid (pLIXSN) was associated with the Neutraplex™ system according to example 2 (Nx1D/pDNA) and example 4 (Nx2D/pDNA) and administered IV via a caudal vein to Black 6 C57 mice. These mice did not develop specific antibodies to human Factor IX. 20 µg of pLIXSN-DNA in the form of Nx1D/pLIXSN-DNA Neutraplex™ complexes were administered per mouse. Blood samples were drawn from the retro-orbital sinus of the mice 2.5 days after injection and placed in tubes containing heparin or citrate and stored at −20° C. hFIX was detected extemporaneously using an ELISA test.

Table 9-1 below summarises the results obtained.

TABLE 9-1

| Formulation | Mouse | hFIX (ng/ml) |
|---|---|---|
| Nx1D/pLIXSN | 1 | 8.6 |
| | 2 | 4.7 |
| | 3 | 5.8 |
| | 4 | 2.3 |
| | 5 | 1.2 |
| | Mean: | 4.5 |
| Nx2D/pLIXSN | 1 | 4.3 |
| | 2 | 18.5 |
| | 3 | 4.4 |
| | 4 | 4.8 |
| | 5 | 2.8 |
| | Mean: | 6.7 |

The results obtained show that injection of either Neutraplex™ preparation induced significant expression of hFIX in circulating blood. The hFIX levels found appear to be 5 to 10 times greater than those found in the past afier gene transfer using synthetic vectors (Baru et al., Gene 161, 143–150, 1995).

Example 10

Neutraplex™ Formulation with Various Nucleic Acids

Neutraplex™ formulations were made with various types of nucleic acids, such as linear double stranded DNA, linear single stranded DNA, RNA and oligodeoxynucleotides (Table 10-1). The nucleic acids were all formulated as previously described in example 2 and all formed stable multilamellar monodisperse particular complexes. The multilamellar structure was still observed by Cryo-EM in these Neutraplex™ complexes several months following preparation, demonstrating their high stability.

TABLE 10-1

| Nucleic acid | size (polydispersity) |
|---|---|
| Linear double strand DNA | 221 nm (0.048) |
| Long Linear double strand DNA | 224 nm (0.198) |
| Linear single strand DNA | 261 nm (0.113) |
| RNA | 188 nm (0.172) |
| Oligodeoxynucleotides | 184 nm (0.045) |

Long linear double strand DNA is the T4 phage DNA (169,372 base pairs). Linear single strand DNA (M13rmp8, 7,229 bases) is the DNA from M13 bacteriophage derivatives. Linear double strand DNA (M13mp8; 7229 base pairs) is the intracellular replicative form of the M13mp8 phage produced by chronic infection in *E. Coli* (Sigma ,St Quentin, France). RNA (ribonucleotide) is the 18S and 28S ribosomal RNA from calf liver (2000 and 5300 bases). ODN is a 27 bases oligodeoxynucleotides. (Xba I, Promega, Wis.).

Example 11

Use of Mono-cationic Lipid Component in Neutraplex™ Formulations

Phosphonolipids such as the dioleoyltrimethylammonium $(C_{18}H_{35}O)_2$—P=O—$N(CH_3)_3$, (GLB.43) and dimyristoyltrimethylammonium $(C_{14}H_{29}O)_2$—P=O—N(CH$_3$)$_3$, (GLB.73) phosphonolipids are monocationic lipids which formed stable monodisperse particles with pDNA (pCMV, 7.2 kb, CLONTECH) when formulated in Neutraplex™ (Table 11-1, Neutraplex™ #1–8). These preparations were added to HeLa cells (2ugpDNA/400,000 cells). Following incubation of two days in serum-containing culture medium, the cells were collected and the β-galactosidase activity was assayed using the Promega Test. The resulting Neutraplex™ showed high transfection efficiency in cultured cells (Table 11-1). Neutraplex™ with negative charge (i.e. Neutraplex™ #4) have under the conditions used in this experiment higher transfection efficacy compared with these with positive charge (i.e. Neutraplex™ #3 pCMVβgal formed stable monodisperse particles. The Neutraplex™ formed showed high transfection efficiency in cultured cells (Table 11-1, Nx4, 6–8). Neutraplex™ particles formulated without a neutral component (Nx5) with the same positive and negative components, and the same quantity of DNA (Nx4, Nx5)showed lower transfection efficacy. In addition, it is noteworthy that the transfection efficiency of positive as well as negative Neutraplexe™ was equal or higher in the presence of serum as compared to the absence of serum (4 hour incubation) indicating their high stability in a biological environement.

TABLE 11-1

| Preparation | Neutraplex ™ component | | | Size (polydispersity) | Zeta Potential (mv) | Transfection (mU of βgal in 50 μL lysate) |
|---|---|---|---|---|---|---|
| | Positive | Neutral | Negative | | | |
| Nx1 | 1.6 mg GL73 | 2 mg DOPE | 0.5 mg Cardio-C14 0.96 mg ADN | 223 nm (0.17) | −65 | 5.5 |
| Nx2 | 1.8 mg GL43 | 1 mg DOPE | 0.5 mg Cardio-C14 0.96 mg ADN | 227 nm (0.12) | −52 | 3.2 (with serum; 0.4 without serum) |
| Nx3 | 1.8 mg GL43 | 1 mg DOPB | 0.5 mg Cardio-C14 0.24 mg ADN | 177 nm (0.15) | +45 | 5.4 |
| Nx4 | 1.8 mg GL43 | 1 mg Chol | 0.5 mg Cardio-C14 0.96 mg ADN | 224 nm (0.11) | −58 | 9.5 |
| Nx5 | 1.8 mg GL43 | | 0.5 mg Cardio-C14 0.96 mg ADN | 206 nm (0.10) | −54 | 1.6 |
| Nx6 | 1.8 mg GL43 | 1.5 mg Chol | 0.65 mg Pserine-C18 0.96 mg ADN | 209 nm (0.28) | −46 | 3.5 |
| Nx7 | 1.8 mg GL43 | 1.5 mg Chol | 0.55 mg Pserine-C14 0.96 mg ADN | 180 nm (0.24) | ND | 1.1 |
| Nx8 | 1.8 mg GL43 | 0.5 mg Chol | 0.5 mg Cardio-C18 0.96 mg ADN | 215 nm (0.09) | ND | 3.1 |

Example 12

Use of Cardiolipin Derivatives and Phosphatidylserine as the Anionic Component in Neutraplex™ Formulations Dioleoyldiphosphatidylglycerol (Cardio-C18) and dimyristoyldiphosphatidylglycerol (cardio-C14) are synthetic Cardiolipin derivatives (Avanti, Ala., USA) and were used in place of the natural extracted Cardiolipin in the Neutraplex™ formulation. Stable complexes were formed with pCMVβgal(Table 11-1, Neutraplex™ #1–5 and 8). The Neutraplex™ formed showed high transfection efficiency in cultured cells.

Dioleoylphosphatidylserine and dimyristoylphosphatidylserine (Pserine-C18 and Pserine-C14, respectively) are anionic phospholipids used in place of the natural extracted Cardiolipin in Neutraplex™ formulation (Table 11–1, Neutraplex™ #6 and 7). Stable complexes were formed with pCMVβgal. The Neutraplex™ particles formed showed high transfection efficiency in cultured cells (Table 11–1).

Example 13

Use of Cholesterol as the Neutral Component in Neutraplex™ Formulations

Cholesterol was used as the neutral component in the Neutraplex™ formulation. The resulting complexes with Example 14

Use of Polymers in Neutraplex™ Formulations

Poly-L-Glutamate (Sigma) of 1000 MW, a negatively charged peptidic polymer containing six charges per molecule, was used in Neutraplex™ formulation in place of the negative constituent. Poly-L-Glutamate was added to the lipid film in 50 or 150 l of 90% ethanol (1 mg/ml).

Glucidex 6 QAE, a cationic polysaccharidic polymer of sixteen sugar units, was derivatized with cations (1.82 mEq/mg). Glucidex 6 QAE was used in Neutraplex™ formulation in place of the positive constituent. It was added to the neutral lipid in 200 l of 80% ethanol (6.6 mg/ml) to form a dried film. SUV were formed following addition of water to the ethanol mixture. pDNA (pCMVβgal) and SUV were diluted in water before mixing. The size distribution and charge of the resulting particles were analyzed by Dynamic Light Scattering with a ZetaSizer 3000 from Malvern.

Some preparations were added to HeLa cell culture and the β-galactosidase activity was determined by spectrometry using the Promega Test (Promega, Paris). Transfection experiments were carried out in duplicate. The results are summarized in Table 14–1:

TABLE 14-1

| Preparation | Composition SUV: Cationic component Neutral component Anionic component (solvent) | DNA | Size (nm) | Polydispersity | Zeta (mV) |
|---|---|---|---|---|---|
| Control 1 | DOGS DOPE In EtOH 90%, H$_2$O 10% | 20 μg DNA | 159.7 | 0.326 | +46.0 |
| Control 2 | DOGS DOPE In EtOH 90%, H$_2$O 10% | 40 μg DNA | 241.3 | 0.330 | +39.8 |
| Control 3 | DOGS DOPE In EtOH 100% | 20 μg DNA | 166.2 | 0.298 | +50.3 |
| Control 4 | DOGS DOPE In EtOH 100% | 40 μg DNA | 217.9 | 0.362 | +41.0 |
| Control 5 | DOGS DOPE In EtOH 100% | 60 μg DNA | 233.5 | 0.437 | +42.0 |
| Neutraplex™ 6 | DOGS DOPE Poly-Glutamic Acid in (150 μl EtOH) | 20 μg DNA | 258.2 | 0.343 | +31.4 |
| Neutraplex™ 7 | DOGS DOPE Poly-Glutamic Acid (in 150 μl EtOH) | 40 μg DNA | 269.1 | 0.509 | −26.0 |
| Neutraplex™ 8 | DOGS DOPE Poly-Glutamic Acid (in 150 μl EtOH) | 60 μg DNA | 227.6 | 0.310 | −35.5 |
| Neutraplex™ 9 | DOGS DOPE Poly-Glutamic Acid (in 50 μl EtOH) | 20 μg DNA | 188.1 | 0.258 | +39.3 |
| Neutraplex™ 10 | DOGS DOPE Poly-Glutamic Acid (in 50 μl EtOH) | 40 μg DNA | 231.0 | 0.380 | −27.5 |
| Control 11 | EtOH 80%, H$_2$O 20% DOPE CL in 50 μl EtOH | 20 μg DNA | ND | ND | −63.8 |
| Control 12 | EtOH 80%, H$_2$O 20% DOPE CL in 50 μl EtOH | 40 μg DNA | ND | ND | −57.1 |
| Control 13 | EtOH 80%, H$_2$O 20% DOPE CL in 50 μl EtOH | 60 μg DNA | ND | ND | −64.3 |
| Neutraplex™ 14 | G6 QAE 1.82 mEq/g(200 μl) DOPE CL in 50 μl EtOH | 20 μg DNA | 354.1 | 0.365 | +56.1 |
| Neutraplex™ 15 | G6 QAE 1.82 mEq/g(200 μl) DOPE CL in 50 μl EtOH | 40 μg DNA | 206.2 | 0.216 | −31.8 |
| Neutraplex™ 16 | G6 QAE 1.82 mEq/g(200 μl) DOPE CL in 50 μl EtOH | 60 μg DNA | 521.0 | 1 | −42.1 |

The data obtained with control preparations 1 to 5 containing no Poly-L-Glutamate showed that no negatively charged particles could be obtained even with the presence of 60 ug pDNA/2 mg lipid. When polyglutamic acid was added (Neutraplex™ preparations 6–10), negatively charged particles appeared, proving the incorporation of polyglutamic acid in the complexes. In contrast, addition of increasing concentration of pDNA correlated with a decrease of the zeta potential indicating the transition to negatively charged particles (Neutraplex™ preparations 6–10). Neutraplex™ formulations #6 and #9 (positively charged) and #10 (negatively charged) resulted in the transgene expression with 3.1, 2.9 and 2.2 mU/ml.

The data obtained with control preparations #11–13 showed that in absence of a cationic constituent, no complexes or particles can be formed. In presence of Glucidex 6 QAE in place of the cationic constituent (Nx4), particulate complexes are formed with DNA. The addition of increasing concentrations of pDNA correlated with a decrease of the zeta potential, indicating the transition to negatively charged particles (Neutraplex™ preparations 14–16).

Example 15

Use of Detergents in Neutraplex™ Formulations

CTAB (Hexadecyltrimethylammonium bromide), a cationic detergent (amphiphile), was used as the cationic component in a Neutraplex™ formulation. When 15 μg and 60 μg pCMVβgal are formulated with 0.8 mg CTAB, 1 mg DOPE and 0.5 mg Cardiolipin, the preparations showed stable and monodispersed particles (222 nm, polydispersity 0.028; and 205 nm, polydispersity 0.172, respectively) and zeta potential of 17 and −37 mV, respectively. The presence of transfected cells were detected by β-galactosidase histochemical analysis.

Lysophosphatidylglycerol, an anionic detergent (amphiphile), was used as the anionic component in a Neutraplex™ formulation. When 15 μg and 60 μg pCMVβ-gal are formulated with 1.8 mg GLB.43, 0.5 mg cholesterol and 0.5 mg lysophosphatidylglycerol, the preparations showed stable and monodispersed particles (196 nm, polydispersity 0.187; and 308 nm, polydispersity 0.186, respectively) and zeta potential of 64 and −8 mV, respectively. The transfection efficiency of the former Neutraplex™ formulations, when adding 60 mg of DNA showed 2.1 mU of β-gal.

Example 16

Use of Nucleoside as the Negative Therapeutic Agent to Deliver in Neutraplex™ Formulation 8-Azidoadenine-5'-monophosphate (AZA) is a nucleoside that is similar to AZT, the antiviral drug used for HIV therapy. Because of its anionic nature (one charge/molecule, 388.2 MW), AZA was formulated in a Neutraplex™ particle as described in example 2 as an example of a biologically active substance used in place of the nucleic acids. AZA diluted in water (5 mg/ml) was added to the vesicules. Results are summarized in Table 16-1.

TABLE 16-1

| Preparation | Neutraplex ™ Composition | Size (nm) | Polydispersity | Zeta (mV) |
| --- | --- | --- | --- | --- |
| Control 1 | AZA 0 μg | 193.5 | 0.465 | +54.5 |
| Neutraplex ™ 2 | AZA 10 μg | 197.4 | 0.427 | +57.8 |
| Neutraplex ™ 3 | AZA 20 μg | 202.3 | 0.417 | +53.1 |
| Neutraplex ™ 4 | AZA 40 μg | 208.1 | 0.323 | +48.8 |
| Neutraplex ™ 5 | AZA 60 μg | 162.6 | 0.290 | +38.8 |
| Neutraplex ™ 6 | AZA 100 μg | 423.1 | 0.395 | +33.2 |

The resulting complexes obtained showed high stability and monodispersed population size when AZA is added. Increasing AZA concentration resulted in decreasing zeta potential demonstrating the increasing incorporation of AZA in the Neutraplex™.

Example 17

Use of Isopropanol as Solvent in the Neutraplex™ Gormulation.

Isopropanol was used as the non-aqueous solvent for the preparation of SUV made from 1.8 mg GLB.43, 0.5 mg cholesterol and 0.5 mg cardio-C14:0. When 15 and 40 μg pCMVβ-gal were mixed with such SUV, stable and monodispersed particular complexes were obtained (231 nm, polydispersity 0.026, 69 mV; and 233 nm, polydispersity 0.114, −27 mV, respectively).

What I claim is:

1. A stable, particulate complex having a global negative or neutral charge, a spherical shape, and a lamellar, rolled and condensed particulate structure, the complex comprising a globally anionic biologically active substance and a mixture of a cationic constituent and an anionic constituent, wherein at least one member of the group consisting of the cationic constituent and the anionic constituent is a lipid.

2. A complex according to claim 1, wherein the complex has a charge ratio of approximately 0.01 to 1.

3. A complex according to claim 1, wherein the complex has a charge ratio of approximately 0.01 to 0.9.

4. A complex according to claim 1, wherein the mixture further comprises a neutral constituent.

5. A complex according to claim 1, wherein the cationic constituent condenses the globally anionic biologically active substance.

6. A complex according to claim 1, wherein the lipid is a phospholipid.

7. A complex according to claim 1, wherein the cationic constituent comprises a lipomonoamine or a lipopolyamine.

8. A complex according to claim 1, wherein the cationic constituent is a non-lipid.

9. A complex according to claim 1, wherein the non-lipid is a polymer or detergent.

10. A complex according to claim 1, wherein the anionic constituent is a non-lipid.

11. A complex according to claim 10, wherein the non-lipid is a polymer or detergent.

12. A complex according to claim 1, wherein both the cationic constituent and the anionic constituent are lipids.

13. A complex according to claim 12, wherein the lipids are phospholipids.

14. A complex according to claim 1 wherein the anionic constituent comprises a diphosphatidylglycerol.

15. A complex according to claim 1, wherein the cationic constituent comprises a lipopolyamine.

16. A complex according to claim 14, wherein the diphosphatidylglycerol is Cardiolipin.

17. A complex according to claim 15, wherein the lipopolyamine comprises DOGS.

18. A complex according to claim 17, wherein the anionic constituent comprises Cardiolipin.

19. A complex according to claim 18, further comprising a neutral constituent.

20. A complex according to claim 4, wherein the neutral constituent comprises a lipid.

21. A complex according to claim 20, wherein the lipid of the neutral constituent is a phospholipid.

22. A complex according to claim 21, wherein the phospholipid comprises DOPE.

23. A complex according to claim 20, wherein the lipid of the neutral constituent is cholesterol.

24. A complex according to claim 19, wherein the neutral constituent comprises cholesterol or DOPE.

25. A complex according to claim 1, wherein the molar ratio of the cationic constituent to the anionic constituent is approximately 0.1:2 to 10:1.

26. A complex according to claim 4, wherein the weight ratio of the cationic constituent to the neutral constituent to the anionic constituent is approximately 1:1:0.1 to 1:1:1.

27. A complex according to claim 1, wherein the globally anionic biologically active substance is a nucleic acid molecule.

28. A complex according to claim 27 wherein the nucleic acid molecule comprises double or single stranded DNA or RNA.

29. A complex according to claim 28 wherein the DNA or RNA comprises an oligonucleotide or ribozyme.

30. A complex according to claim 1, wherein the globally anionic biologically active substance comprises heparin or a ganglioside.

31. A complex according to claim 1, wherein the globally anionic biologically active substance comprises a chromosome or a fragment of a chromosome.

32. A complex according to claim 1, wherein the globally anionic biologically active substance comprises a procaryote genome or a fragment of a procaryote genome.

33. A complex according to claim 1, wherein the globally anionic biologically active substance comprises a viral genome or a fragment of a viral genome.

34. A complex according to claim 1, wherein the globally anionic biologically active substance comprises a protein, peptide, glycopeptide, lipoprotein, glycolipid, nucleoside, hormone or vitamin.

35. A complex according to claim 1, further comprising a compatible medium for pharmaceutical use.

* * * * *

UNITED STATES PATENT AND TRADEMARK OFFICE
CERTIFICATE OF CORRECTION

PATENT NO. : 6,096,335
DATED : August 1, 2000
INVENTOR(S) : Alain R. Thierry

It is certified that error appears in the above-identified patent and that said Letters Patent is hereby corrected as shown below:

Column 3,
Line 19, now reads "vilvo" should read -- vivo --

Column 10,
Line 35, now reads "Neutraplex™ The" should read -- Neutraplex™. The --

Column 12,
Line 28, now reads "Neutrapl™ Complexes" should read -- Neutraplex™ Complexes --

Column 15,
Line 18, now reads "Neutraplxrm" should read -- Neutraplex™ --

Column 18,
Line 10, now reads "Neutraplex™" should read -- Neutraplexes™ --

Signed and Sealed this

Fourth Day of September, 2001

Attest:

*Nicholas P. Godici*

NICHOLAS P. GODICI
*Attesting Officer*   *Acting Director of the United States Patent and Trademark Office*